United States Patent [19]

Mintz

[11] Patent Number: 4,551,308
[45] Date of Patent: Nov. 5, 1985

[54] APPARATUS FOR ANALYZING THE INFLUENCE OF ADDITIVE REAGENTS UPON THE COAGULATION OF BLOOD AND RELATED METHODS

[75] Inventor: Michael D. Mintz, Edison, N.J.

[73] Assignee: International Technidyne Corp., Edison, N.J.

[21] Appl. No.: 549,070

[22] Filed: Dec. 23, 1983

Related U.S. Application Data

[62] Division of Ser. No. 281,661, Jul. 9, 1981, Pat. No. 4,443,408.

[51] Int. Cl.$^4$ ................. G01N 21/03; G01N 21/75; G01N 33/86
[52] U.S. Cl. ........................... 422/58; 215/6; 356/246; 366/336; 422/73; 422/102; 436/69; 436/165
[58] Field of Search ................. 366/336, 337, 340; 215/6; 356/246, 427; 128/760; 604/403; 422/58, 102, 209, 73; 436/165, 69

[56] References Cited

U.S. PATENT DOCUMENTS

| | | | |
|---|---|---|---|
| 3,871,770 | 3/1975 | von Behrens | 356/246 X |
| 4,070,249 | 1/1978 | Janin et al. | 366/336 X |
| 4,313,680 | 2/1982 | Honnen | 366/337 |
| 4,411,518 | 10/1983 | Meserol et al. | 356/246 X |

FOREIGN PATENT DOCUMENTS

| | | | |
|---|---|---|---|
| 3104796 | 9/1982 | Fed. Rep. of Germany | 356/246 |
| 0116262 | 9/1980 | Japan | 422/102 |

*Primary Examiner*—Arnold Turk
*Attorney, Agent, or Firm*—Arthur L. Plevy

[57] ABSTRACT

A sample of blood is divided into a plurality of isolated test chambers. The blood is mixed with additive reagent having previously been measured into each test chamber. A clot detector and analyzer system determines the time required for the blood-reagent mixture in each chamber to form a clot. In a first mode of analyzer system operation there is recorded the time required for a selected number of clots to be detected. A second mode of operation identifies those chambers in which clots have been detected within a specified time interval.

4 Claims, 13 Drawing Figures

APPARATUS FOR ANALYZING THE INFLUENCE OF ADDITIVE REAGENTS UPON THE COAGULATION OF BLOOD AND RELATED METHODS

This is a divisional of application Ser. No. 281,661, filed on 7/9/87 and now U.S. Pat. 4,443,408 issued on Apr. 17, 1984.

BACKGROUND OF INVENTION

This invention relates to the analysis of blood coagulation time as it is influenced by differing concentrations of additive reagents, and more particularly to apparatus and methods for performing the analysis of blood coagulation time.

It is well-known in the practice of clinical medicine to inhibit the coagulation of blood by administering various anticoagulant medications. One such medication, heparin, is particularly important because its effects as well as its neutralization by the agent, protamine, are essentially instantaneous. Widely used in early treatment of thromboembolic disease, herapin's most noteworthy applications are in the fields of extracorporeal circulation such as cardiovascular surgery and hemodialysis. An excellent article giving a survey of the herapin therapy field is entitled "Inappropriate Response to Herapin" by H. B. Soloway, Diagnostic Medicine, Sept./Oct. 1979, pages 31-33.

Protocols for heparin therapy administration and control are usually based upon a prescribed prolongation of coagulation time as determined by some clot timing technique. Protocols which prescribe a heparin dose based upon patient's sex, weight and height fail to account for variations in patient response to herapin. Such problems and a proposed solution are discussed by Bull, et al., "Heparin therapy during extracorporeal circulation: I. Problems inherent in existing heparin protocols; II. The use of a dose-responsive curve to individualize heparin and protamine doseage," 69 J. Throacic Card. Surg. 674-689 (1975). Application of the method of Bull, et al to the system described in U.S. Pat. No. 3,695,842 issued to Michael D. Mintz, the inventor herein, is explained by Kersting and Rush, "A Simple Individualized Method for Dose-Responsive Heparin and Protamine Administration," 11 J. Extra-Corp. Tech. 56-60 (1979). Briefly described, the dose-responsive technique is an in vivo method in which coagulation time tests are performed on blood samples taken before and after a patient has been given one or two bolus heparin infusions. The resulting data, plotted as heparin vs coagulation time, are used to determine current heparin level, maintenance dose requirement and protamine neutralization dose implied by subsequent coagulation time tests.

U.S. Pat. No. 4,000,972 entitled MEASURING SYSTEM FOR THE PHARMACOLOGICAL MANIPULATION OF THE COAGULATION MECHANISM IN BLOOD AND FOR THE ELAPSED COAGULATION TIME issued to Braun, et al. on Jan. 4, 1977, describes a system and method of protamine titration of heparin-medicated blood in which a single blood sample is divided into a plurality of test chambers. Thereafter, differing amounts of protamine are injected into each chamber and mixed with the blood aliquots. The test is terminated upon first observation of clotting in one of the chambers. The protamine concentration in the chamber thus identified is designated by the system as the neutralizing protamine concentration. A calculator section of the system subsequently interprets this data, in conjunction with certain operator-input patient and protocol data to yield the patient's specific protamine dose requirement. By equating the neutralizing protamine concentration to heparin concentration and comparing this implied level of heparinization with the operator-input, heparin maintenance level, the calculator section computes a heparin make-up dose for the patient. This prior art system has the advantages of performing analyses on a single sample of blood. Test results are essentially independent of the temperature conditions to which the various test chambers are simultaneously subject, and they are readily understood by the operator.

The system of Braun, et al. has several disadvantages. First, the coagulation time reported by the analyzer is representative of the neutralized sample after addition of protamine, not of the blood as it may be flowing in patient or extracorporeal circuit. Second, the basis for selecting the first observed clotted chamber as that containing the exact neutralizing protamine concentration is, as stated by the inventors, "too much protamine results in anticoagulated blood." While this statement is generally accepted as factual for large concentrations of protamine, Perkins, et al., "Neutralization of heparin invivo with protamine; A simple method of estimating the required dose", 48 J. Lab. & Clin. Med. 223-226 (1956) has shown that protamine concentrations of as much as three times the neutralizing concentration in heparinized blood may exhibit essentially identical coagulation times. In-as-much as all clot detectors are characterized by some degree of statistical uncertainty, it will be seen that the first clotted blood specimen in this prior art system may randomly contain protamine concentrations between one and three times the desired levels.

Another disadvantage of this prior art system is that it is limited to use in heparin therapy protocols that seek to maintain or control heparin concentration. It has been shown by several researchers (see for example, Berg, et al., "Monitoring heparin and protamine therapy during cardiopulmonary bypass by activated clotting time" 11 J. Ext. -Corp. Tech. 229-235 (1979), however, that the heparin dose required to prolong coagulation to a specific activated clotting time value of say 480 seconds may vary from 100 to 700 units per kilogram of body weight. Hence, control of blood heparin concentration alone may be inadequate to prevent clotting during critical extracorporeal procedures.

OBJECTS OF THE INVENTION

Accordingly, it is the object of the present invention to provide an improved apparatus for reliably measuring coagulation time, determining the heparin concentration in blood necessary to prolong coagulation time to specified values, and determining the protamine concentration required to neutralize the heparin in heparinized blood.

It is a further object of the present invention to provide apparatus for monitoring and controlling heparin therapy that are compact, easily operated and easily interpreted by the operator.

These and other objects relate to an improved apparatus which is easy to use and fabricate as well as efficient methods for performing such measurements.

SUMMARY OF THE INVENTION

A system and method of analyzing the influence of coagulant and anticoagulant reagents or medications on the coagulation time of blood. The foregoing objects are obtained in accordance with the present invention whereby a sample of blood, normal or anti-coagulated, is divided by known volumes into a plurality of numbered test chambers comprising a test cartridge, there having been previously measured into each test chamber coagulant or anti-coagulant reagents such that the reagent concentration of the blood-reagent mixture in a chamber may be calculated by multiplying a predetermined numerical constant and the assigned cell number.

According to the present invention a simple timer or stop watch is activated by an operator when the cartridge and blood-reagent mixture is in a condition ready to start the analysis and the test cartridge is manually agitated. Upon elapse of a predetermined or given time interval each test chamber of the cartridge is inspected for clotted blood. The results, identified by chamber number, are recorded. If, for example, the premeasured reagent is an anti-coagulant, the concentration of such anti-coagulant required to prolong coagulation to at least the given time interval is obtained by identifying the lowest numbered test chamber in which no clot has been observed. The mathematical product of the chamber number thus identified and the predetermined constant manifests the required anti-coagulant concentration.

Another aspect of the present invention provides a multi-chamber test cartridge which is inserted into an automatic analyzer system. The system includes a plurality of data channels each associated with a separate clot detector, electronic memory latch and a visual panel display indicator. Each chamber of the test cartridge is cooperative with one channel of the analyzer and is uniquely identified on the panel display. A blood level detector is provided to start the analysis when it is sensed that all of the test chambers have been filled with the required volume of blood. An electric motor coupled to the test cartridge provides mechanical rotation to mix the blood and reagent in the various test chambers. A timer and timer panel display provides timed control functions and readout during the analysis. An end point counter maintains a record of the number of test chambers in which clots have been detected during the analysis.

Digital comparators continuously compare timer and end point counter data with operator selected panel switch settings, thereby to select the analyzer mode of operation and operating parameters.

The analysis is preceeded by the operator selecting panel switch settings and test chamber reagents according to a desired procedure. The test cartridge with premeasured reagents is then placed in the analyzer instrument. A sample of medicated or normal blood is thereafter injected into the test cartridge, where it is automatically divided into the various individual test chambers. On filling all of the test chambers the blood overflows into an auxillary chamber where it is sensed by the blood level detector. The resulting signal initiated by the blood level detector causes the latches and timer to be reset and the timer to start timing the analysis. The reset logic enable latch causes the clot detectors to be activated and energizes the motor, which agitates the test cartridge causing the blood and reagent in each chamber to be mixed. The first time a clot is detected in a given test chamber, the corresponding panel display indicator is energized and the end point counter incremented. The analysis is terminated when either the timer or the end point counter comparators register equality with corresponding panel switch settings.

The following table summarizes analytic capabilities of the apparatus which are important in maintaining control of heparin anti-coagulant therapy during surgical procedures.

| Analysis | Reagent | End of Analysis Condition | Interpretation |
|---|---|---|---|
| Average coagulation time | none | End point counter has counted clots in half of total test chambers | Approximate average coagulation time displayed by timer panel display |
| Heparin concentration requirement | heparin | Timer registers perscribed time interval for coagulation prolongation | Required heparin concentration equal to product of lowest chamber number not registering clot on panel indicators and predetermined numerical constant |
| Protamine concentration required to neutralize heparin in heparinized blood | protamine | Timer registers time interval equal to predetermined normal or unheparinized coagulation time for the same blood as determined by prior analysis | Required protamine concentration approximately equal to product of lowest chamber number registering clot on panel indicators and predetermined numerical constant |

DETAILED DESCRIPTION OF THE INVENTION

Figure 1:
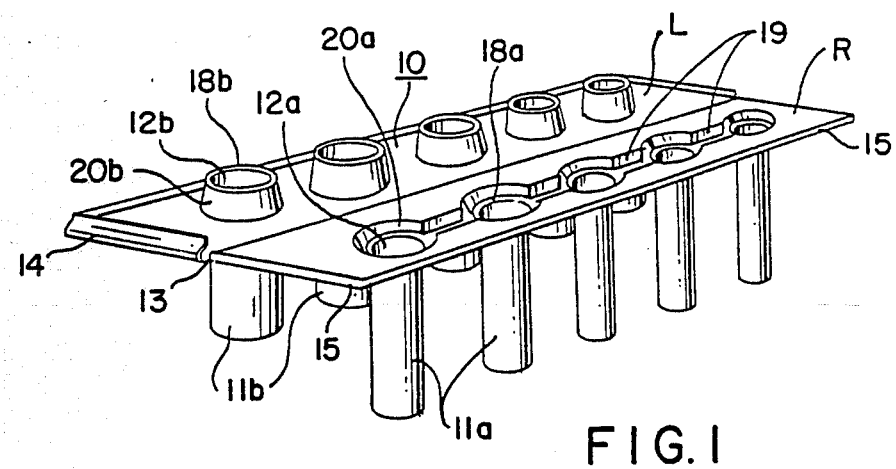
FIG. 1 is a perspective view of a first embodiment of the invention illustrating a one-piece test cartridge comprising five test chambers.

Referring to FIG. 1, there is shown a cartridge assembly 10 which can be used to analyze the coagulation time of blood when subjected to an additive reagent.

A base plate is divided into two sections as a right (R) and a left section (L) by means of a longitudinal groove 13. Located on the right side of the groove 13 are a plurality of first cylindrical chambers or members 11a. Located on the left side (L) of the groove 13 are a second plurality of cylindrical chambers or members 11b.

In FIG. 1, there is shown five chambers designated as 11a and five associated chambers designated as 11b. It is of course understood that the number of such chambers may be varied and hence more or less than five chambers can be included. However, as will be explained, each chamber as 11a is associated with a corresponding chamber as 11b. The chambers 11a have a top depression 20a with sloping sidewalls which is adapted to receive the extending tapered cylindrical flange 20b associated with each chamber on the left side as 11b. The depressions associated with chambers 11a communicate with one another by means of a surface channel 19 which acts as a trough for a blood sample to be received by the assembly as will be explained.

In this manner, upon folding or pivoting the cartridge 10 about the groove 13, each section 20b of cartridge 11b is inserted into the corresponding depression of its associated chamber 11a. To hold the assembly in the folded position, an extending seal 14 is disposed about one section of the assembly 10 R or L and serves to lock or hold a cartridge assembly in position whereby the volume 12a and 12b of each chamber communicate with one another. The seal 14 coacts with the edge 15 on the opposite section. The entire assembly shown in FIG. 1 can be fabricated from a semi-rigid transparent plastic and formed as an integral unit.

Figure 2A:
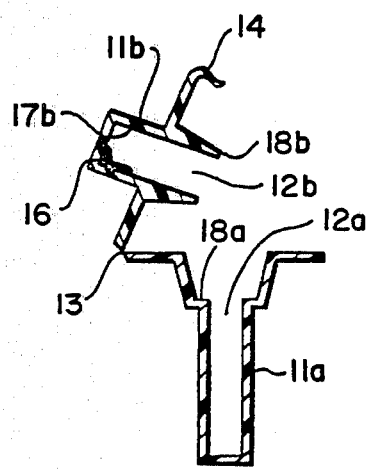
FIG. 2A is a cross-sectional view of the cartridge of FIG. 1 showing one chamber, with the cartridge in a partially closed condition.
Figure 2B:
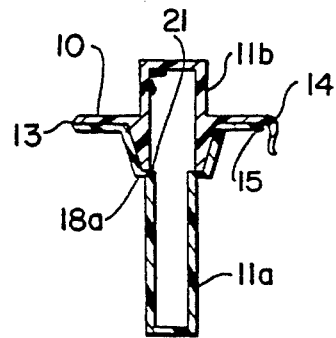
FIG. 2B is a cross-sectional view of the cartridge of FIG. 1 showing one chamber, with the cartridge in a closed condition.

Referring to FIG. 2B, there is shown a transverse cross sectional view of the cartridge 10 depicting members 11a and 11b in a partially closed position. FIG. 2B depicts the members 11a and 11b in a fully closed position with seal 14 coacting with edge 15 to provide the locked state. In FIG. 2A numeral 16 references a premeasured additive reagent applied to to the inner surface 17b of chamber 11b.

As can be ascertained from FIGS. 2A and 2B, the inner diameter 12b of member 11b is somewhat larger than the inner diameter 12a of chamber 11a. In this manner, a peripheral shelve 21 is formed during the closed position as shown in FIG. 2B.

Referring to FIGS. 3A to 3D, there is shown a series of schematic diagrams which depict the sequential operation of the above described apparatus in performing a measurement of coagulation time. In the figures the chambers 11a and 11b are shown generally in cylindrical form and the exact details as described in FIGS. 1 and 2 regarding the depressions and flanges have been omitted for the sake of clarity. In any event, the same reference numerals are employed to designate corresponding structure.

Figure 3A:
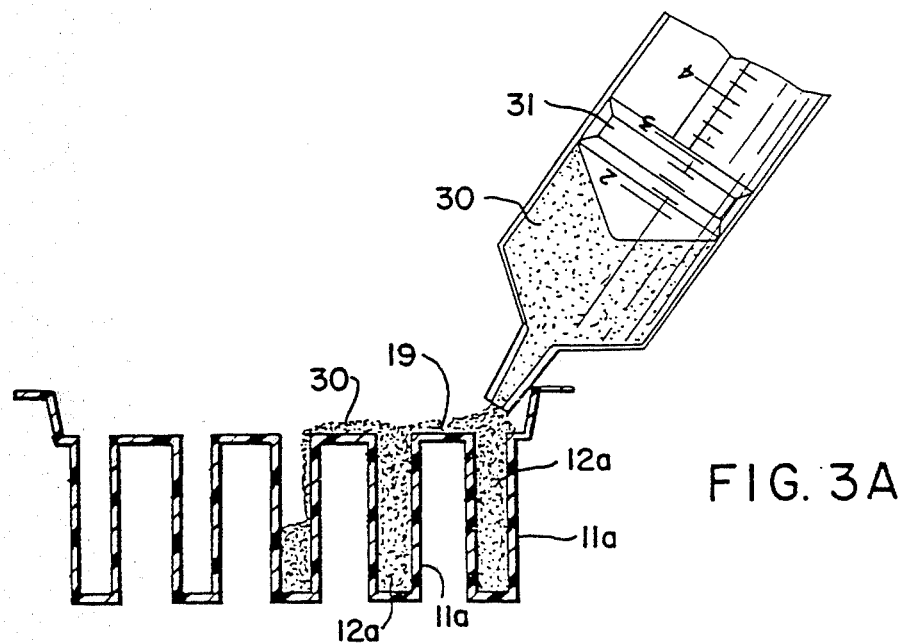
FIG. 3A is a cross-sectional view of the test cartridge of FIG. 1 showing the process of injecting a blood sample.

Referring to FIG. 3A, there is shown a cross-sectional view of cartridges on the right side as 11a. A quantity of heparinized blood sample 30 is injected by means of a syringe 31 into one of the test chambers 11a. As the test chamber is filled, the blood overflows and is directed via the trough 19 into the adjacent test chamber which then becomes filled with the heparinized blood sample. Thus this process is continued until all chambers are filled via the above described action.

Figure 3B:
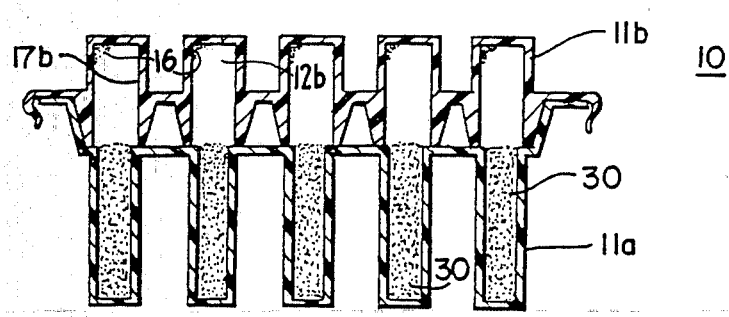
FIG. 3B is a cross-sectional view of the test cartridge of FIG. 1 showing the test chambers closed immediately following blood sample injection.

Once this occurs, the cartridge 10 is closed as shown in FIG. 3B with the inner volume of members 11a communicating with members 11b. The cartridge assembly 10 is then locked by means of seal 14 to form a liquid type barrier as depicted in FIG. 3B.

Also shown in FIG. 3B is the additive reagent 16 which is secured to the inner surface of members 11b as explained. The reagent 16 in each associated chamber 11b is premeasured in incremental quantities and secured to the wall by a vacuum drying technique or other suitable method.

Figure 3C:
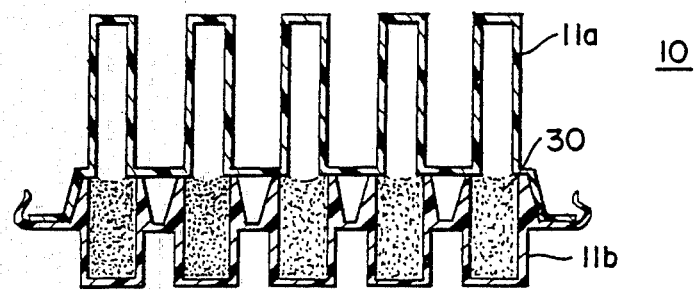
FIG. 3C is a cross-sectional view of the test cartridge of FIG. 1 showing the cartridge inverted for timing an analysis.
Figure 3D:
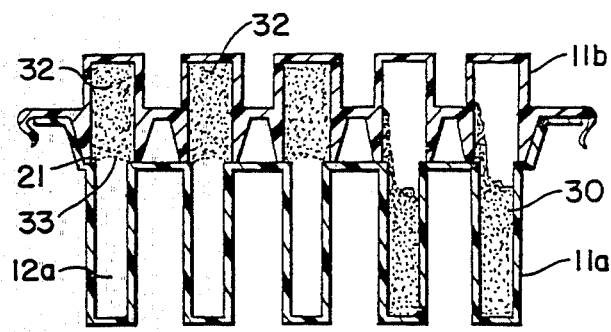
FIG. 3D is a cross-sectional view of the test cartridge of FIG. 1 showing the cartridge in its upright orientation with clotted blood in some of the test chambers at the conclusion of the analysis.

The user then inverts the locked assembly 10 as shown in FIG. 3C and agitates the assembly for several seconds to cause the blood 30 to rapidly flow between the volumes of the coacting chambers. A timer which may be a stop watch or other conventional device is simultaneously started at the commencement of the agitation procedure. The agitation causes the blood in chambers 11b to react with the reagent 16. The time interval selected for analysis is a prescribed interval which is selected by the operator according to a desired procedure to be performed. At the conclusion of this time interval, the cartridge is again inverted as shown in FIG. 3D and hence chambers 11a are in the lower most position. Blood that has clotted (reference numeral 32) is now unable to flow into chambers 11a due to the mechanical bridging at the blood-air interface 33 as supported by the shelf 21 which is analogous to the annular ridge 18a of FIG. 2A and 2B.

It will be understood that additive reagent 16 may be provided in prepackaged form as a freeze-dried or evaporation dried material that is readily soluable in blood and affects the coagulation time of blood 30. Such materials may for example include heparin, protamine, sodium-citrate or calcium chloride. In the case of anticoagulants such as heparin the prescribed time interval of the analysis might be 480 seconds, as recommended by Bull, et al. In such example the test chamber containing a blood-heparin mixture adequate to prolong coagulation to at least the 480 seconds is that chamber containing the least amount of heparin for which no clotted blood is observed after the 480 second interval. If a neutralizing protamine concentration is sought the prescribed time interval of the analysis might be a typical activated coagulation time of 135 seconds. At the conclusion of such time interval the neutralizing protamine concentration is that contained in the test chamber having the lowest protamine concentration in which clotting is observed.

It will be recognized in both the examples of anticoagulant and neutralizing reagent additives that the (analyist) may simply determine patient dose by forming the mathematical product of chamber number, patient blood volume and a constant. The constant in such case is the incremental additive concentration in the test chambers of the cartridge. That is, the blood reagent concentration in chamber 1 is one constant, the concentration in chamber 2 is two constants, etc. Such constants are well-known in that a user would know how to select the constant.

Figure 4:
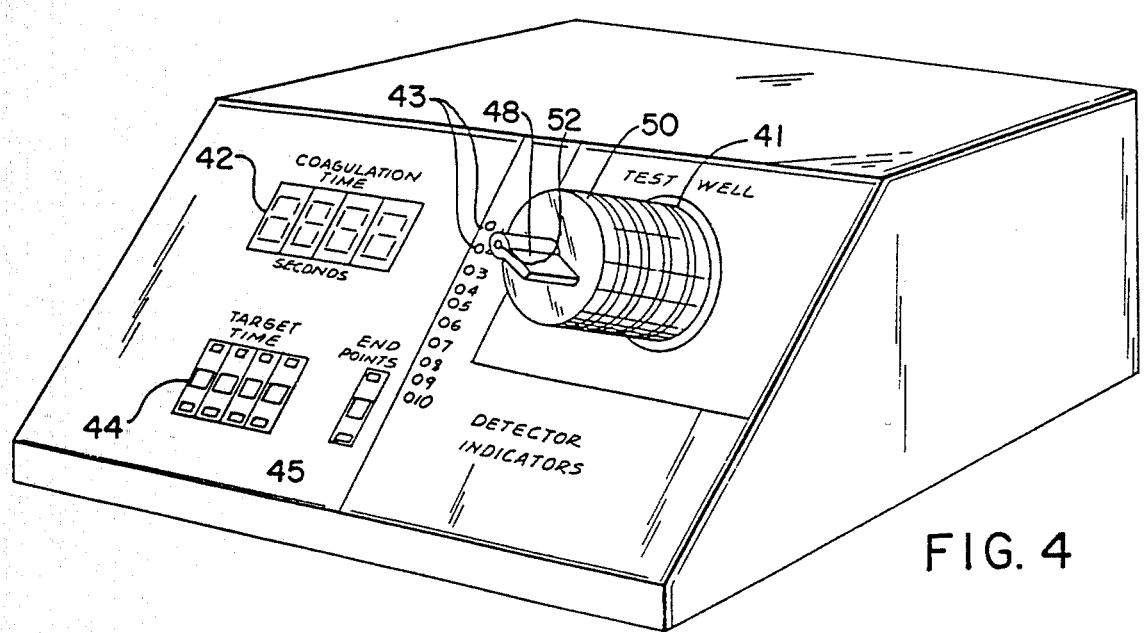
FIG. 4 is a perspective view of a second embodiment of the invention illustrating the analyzer with a test cartridge partially inserted in the test well.

Referring to FIG. 4, there is shown a housing including a front panel configuration of automatic apparatus which will perform a blood coagulation measurement employing a similar method as above described. As will be explained, the automatic test apparatus employs a unique test cartridge 50 which is inserted into a test well 41 associated with the analyzer housing. The front panel of the analyzer includes a digital display 42 which may consists of a seven segment LED or LCD module capable of displaying the running time during an analysis. Also located on the front panel are a plurality of visual indicators 43 which, as will be described, indicate the status of detected clots in various test chambers.

In this manner, the display 43 will indicate the exact test chamber in which a clot occured during a test procedure. Also depicted is a bank of thumb wheel switches 44. As will be explained, the switches 44 are BCD coded to allow a direct interface with the electronic circuitry of the analyzer. The switches 44 are set by the operator or user to specify a given time interval during which the analysis is to be performed.

Another switch 45 is also a thumbwheel switch and has ten positions. The switch 45 is decimally coded to interface with the corresponding circuitry. The operator uses switch 45 to set the switch to a number from 1 to 10(0) to thereby select or establish an analysis completion criterion which terminates the operation of the analyzer when the total number of channels identifying clots in the respective test chambers equals the switch setting.

As seen in FIG. 4, the cartridge 50 has an input aperture 52 for permitting entry of a syringe. The aperture 52 is integrally formed with an outstanding tab 48. The tab 48 will extend from the well 41 to allow a user to remove the cartridge 50 when it is fully inserted into the test well 41.

Figure 5A:
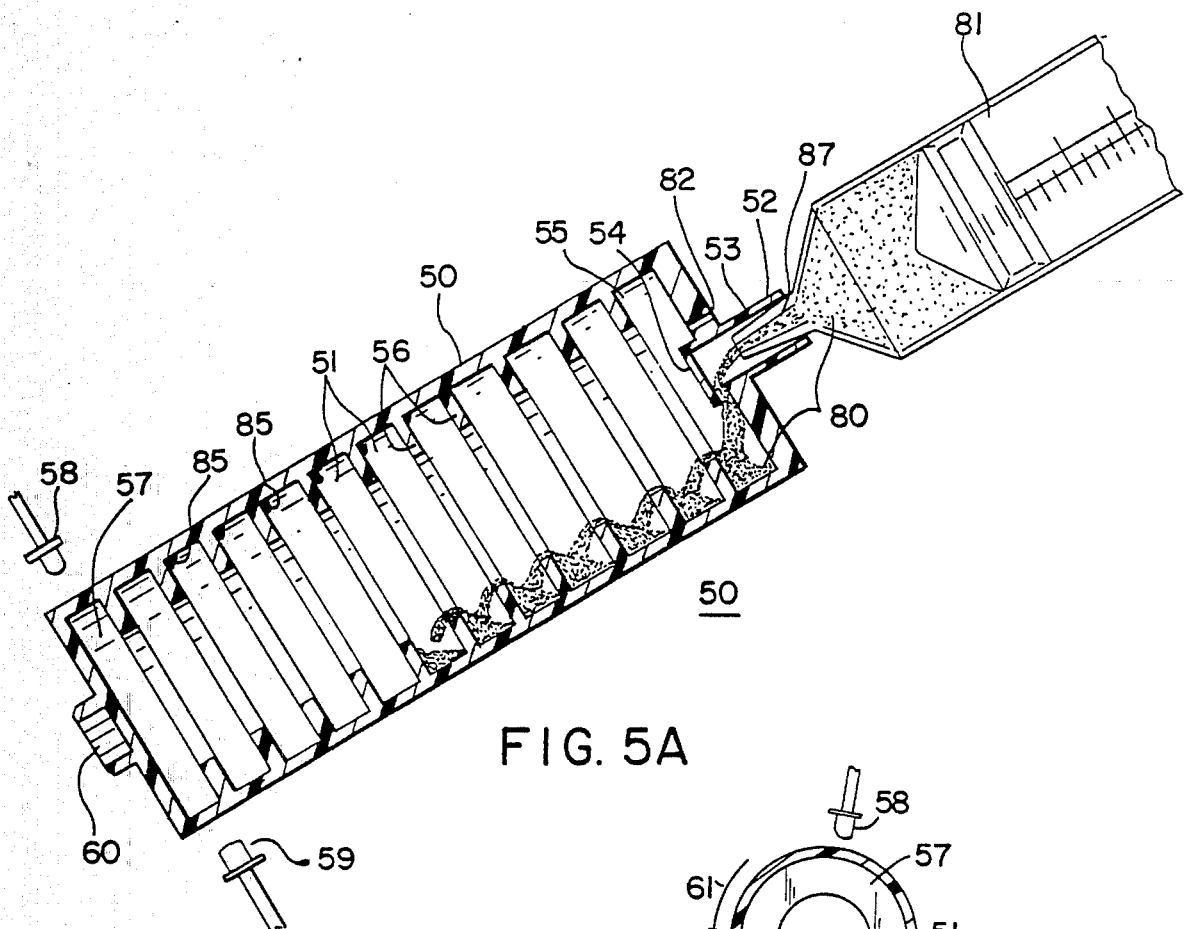
FIG. 5A is a cross-sectional view of the test cartridge of the second embodiment showing the process of dividing the sample as it is injected into the cartridge.

Referring to FIG. 5A, there is shown a longitudinal cross-sectional view of a test cartridge as 50. The cartridge 50 is fabricated from a transparent rigid plastic and has a plurality of coaxial annular test chambers as 51. Each test chamber 51 is separated from an adjacent chamber by means of annular walls 56. Thus as seen from FIG. 5, the test cartridge 50 provides a plurality of individual test chambers.

A blood sample 80 is injected by means of a syringe 81 which is inserted into the aperture 52. The aperture 52 has a tapered inner surface 53 to engage with the Luer-fitting syringe nozzle 87. A baffle 54 is located about the aperture 52 and operates to divert the blood sample 80 to restrict flow into the first input chamber or entry chamber 55.

As can be seen from FIG. 4, the cartridge 50 is emplaced in the well 41. It is held at an angle to allow blood to flow from one chamber to the next under the influence of gravity.

In this manner, the annular walls 56 separate blood into the respective test chambers as 51. A last blood chamber is designated as chamber 57 and is associated with a light source 58 on one side and a photo sensor 59 on the other side.

As one can ascertain, a quantity of blood which enters chamber 57 will serve to blocklight from source 58 to thereby provide an indication that all chambers 51 above chamber 57 have been filled with a blood sample. Also shown associated with cartridge 50 is keyed cavity 60. The cavity 60 is provided to engage a rotational drive means associated with a motor and hence to rotate the cartridge 50 about its axis. There are many techniques for providing a rotational motion to a cartridge as 50 contained within a cylindrical cavity as test well 41.

Also depicted in FIG. 5A is a vent or aperture 82. The aperture 82 allows air to escape from the confines of the cartridge 50 as blood is being injected. The release of air in this manner prevents blood from squirting out or being thrusted out of the main aperture 52.

Figure 5B:
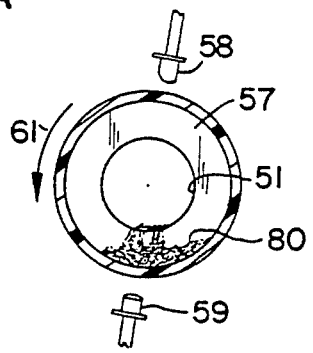
FIG. 5B is an internal view of the test cartridge of the second embodiment showing auxillary or overflow chamber, its relationship to the blood level detector and blood entering the chamber.

Referring to FIG. 5B, there is shown a cross-sectional view of the overflow chamber 57 with blood sample 80 blocking the light projected from source 58 to the photo sensor 59. This, as will be explained, provides a signal which causes the analyzer to begin operation.

Figure 6A:
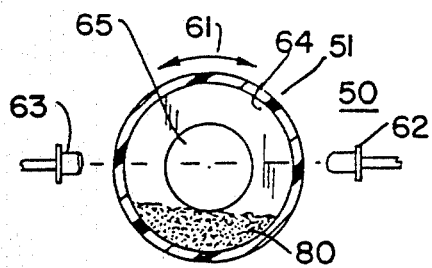
FIG. 6A is an internal view of the test cartridge of the second embodiment showing a test chamber, its relationship to the clot detector and an unclotted blood sample within the chamber.

Referring to FIG. 6A, there is shown a cross-sectional view of a typical test chamber 51 with a blood sample 80 in the lower position. Each chamber as 51 is associated with a separate light source as 62 and a separate photo sensor as 63. As indicated, the cartridge 50 is transparent and in the position shown in FIG. 6A, light emanating from source 62 impinges upon the photo sensor 63.

In FIG. 5A the upper walls of each chamber of the test carriage 50 have secured thereto a predetermined amount of a dried reagent as 85. The amount of reagent in each test chamber varies incrementally as described above. Hence as the cartridge 50 is rotated, the blood sample 80 will contact the reagent 85 and mix therewith.

Figure 6B:
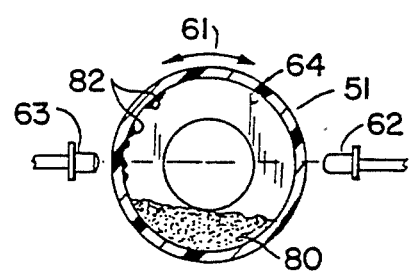
FIG. 6B is an internal view of the test chamber of FIG. 6A showing the chamber, its relationship to the clot detector and a partially clotted blood sample within the chamber.

Referring to FIG. 6B, a rotation in the direction of arrow 61 may be clockwise or counter clockwise. Clotted portions 82 of blood sample 80 are, by natural or surface roughness adhesion processes, caused to adhere to the inner surface 64 of the test chamber wall. The rotation 61 causes the clotted blood 82 to be drawn up and operates to effectively block the light from source 62. Thus, the blocking of the light indicates the presence of a clot and this condition is detected by the electronic assembly of the analyzer as will be explained in detail by referring to FIG. 7.

Figure 7:
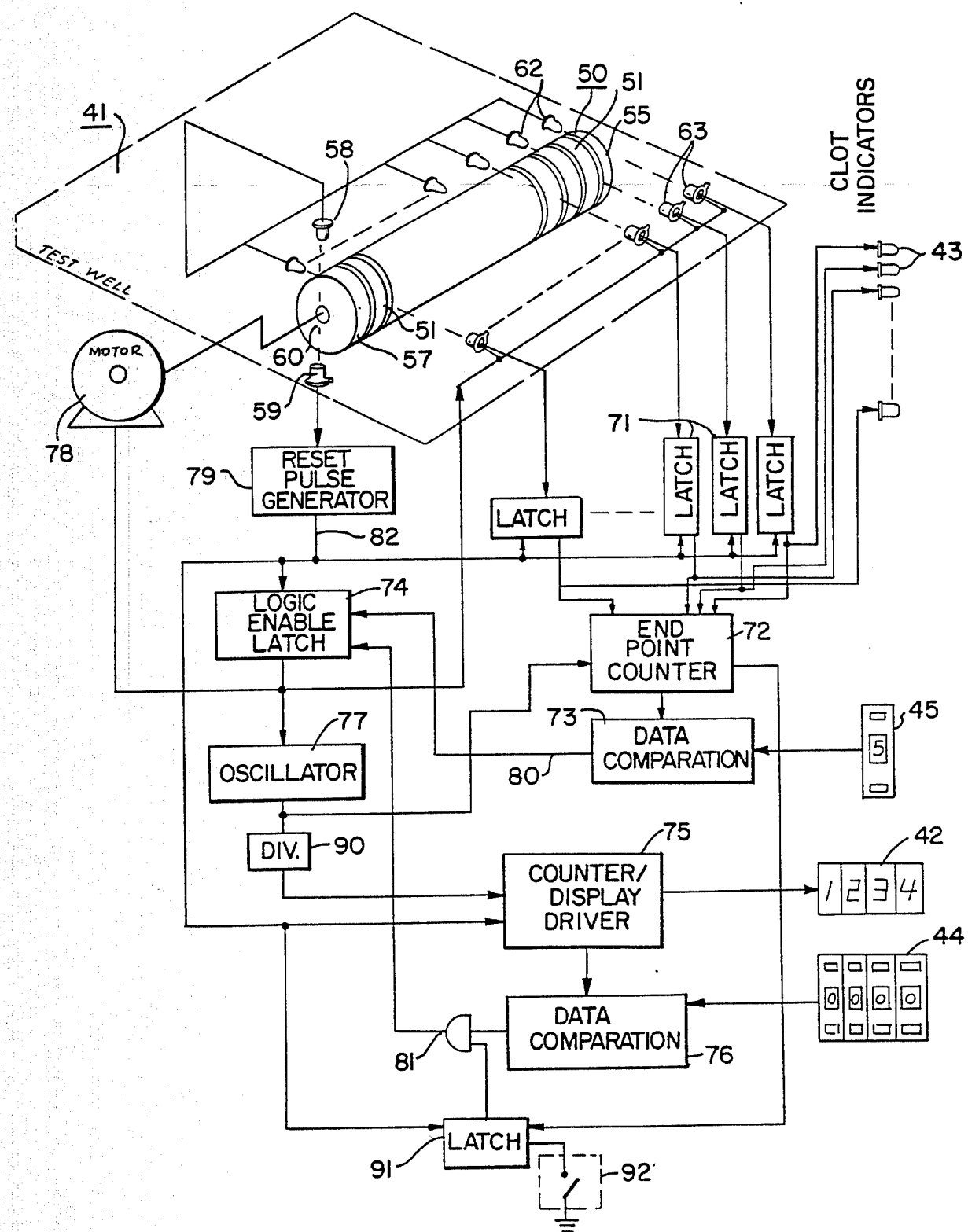
FIG. 7 is a schematic block diagram showing the electronic logic of the analyzer of the second embodiment of the present invention.

FIG. 7 is a schematic block diagram depicting the electronic logic of the analyzer system as for example, included in the housing of FIG. 4. Shown in FIG. 7 is a schematic representation of the test cartridge having the plurality of test chambers 51. The cartridge 50 is inserted into a well which may comprise a cylindrical cavity for receiving the cartridge. Located adjacent each test chamber as 51 is a series of light sources 62 and associated photosensors 63. In this manner each test chamber as associated therewith has its own light source as 62 and an associated sensor 63. Each photosensor is coupled to a respective latch 71.

Essentially, the latch is a bistable circuit which will produce one logic value during a change in impedance of the sensor 63 due to the blockage of light. The latch operates to store this change of state until it is reset.

There are many examples of data latches as 71 known in the art and which will operate in conjunction with photosensors to provide one output such as a logic 1 for the blockage of light and another output such as a logic 0 when light propogates to the sensor 63 via the source 62. The output of each latch is coupled to an end point counter 72. The counter 72 operates to monitor each latch to determine whether there is a change of state. This is easily implemented by means of suitable decode gates associated with counter 72 and responsive to the output state of latches as 71. A data comparator 73 has one input coupled to the counter 72 and one input coupled to the thumbwheel switch 45. The output from switch 45 constitutes ten parallel lines each indicative of one setting as 1 to 10(0). Hence, the comparator 73 will provide an output on lead 80 when the comparator detects a condition where the number of latches 71 designating a clotted sample equals the number programmed into the comparator 73 via switch 45. For the setting shown when five test chambers 51 of the cartridge 50 have clotted samples the data comparator 73 will provide an output on lead 80. The lead 80 is coupled to a logic enable latch 74.

As seen from FIG. 7 the end point counter 72 receives a high frequency scanning pulse train from oscillator 77. Oscillator 77 may be a high speed astable multivibrator. In this manner the end point counter interrogates each latch as 1 to 10(0) in sequence in a rapid manner. Each time a latch changes state and goes from a no clot to a clot position, the counter increments by one count and therefore during a scanning period will detect the number of latches as 71 which change data. Each latch is also coupled and associated with a respective clot indicator 43. The indicators 43 as shown in FIG. 7 and in FIG. 4 may be LED devices or any other suitable device to give an indication of which test chamber provided a clot. The oscillator 77, as will be explained is activated by the logic enable latch 74 which also serves to activate the motor 78.

The motor 78 is mechanically coupled to the keying member 60 of the cartridge 50. The motor 78 operates at a relatively low RPM which may for example, be 0.1 RPM to rotate the cartridge upon activation. The output of the oscillator 77 is also divided by means of a binary divider 90 which may comprise a series of cascaded binary multivibrators to provide a clock signal to display driver 75. Essentially, the counter and display driver 75 receives the clock signal from divider 90 and counts in seconds. In this manner, if the input to the counter and display driver 75 is a 1 Hz waveform, the counter will count in seconds. One output of the counter and display driver 75 is coupled to a digital display 42 which may be an LED or LCD display and will display seconds in a direct digital readout. Another output from counter 75 is directed to one input of a second data comparator 76. The comparator 76 receives other inputs from the thumbwheel switch 44.

Switch 44 is a series of four thumbwheel switches which are coded and which enable the operator to select any predetermined time period as for example, from 0000 to 9999 seconds. The data comparator 76 will compare the time stored in counter 75 with the setting of the thumbwheel switch bank 44 and will provide an output to trigger the enable latch 74 if any clot was detected during this time interval. For example, as seen in FIG. 7 there is shown a latch 91 which receives a trigger input from the end point counter 72. This signal to latch 91 is the clot input signal and will trigger latch 91 whenever any clot is detected.

The triggering of latch 91 enables ANDgate 81 which therefore allows the data comparator 76 to effect the latch 74. The switch 92 may be included to automatically set latch 91 so that gate 81 is always enabled to thereby allow the latch 74 to be triggered by either the data comparator 73 or data comparator 76. Also shown in the circuitry is a reset pulse generator 79. The generator 79 is associated with chamber 57 of cartridge 50 and this will produce a pulse when light source 58 is blocked from sensor 59 during the filling of the cartridge 50 with a blood sample. As soon as blood enters chamber 57 the reset pulse generator 79 produces an output pulse which initially resets latches 71, latch 91 and counter display driver 75 to the all zero state or the reset state to enable the start of a test procedure. The pulse generator 79 also triggers the latch 74 which now energizes the photosensors 63 and applies operating power to the motor 78.

The above described logic diagram may be implemented in many ways as should be understood by those skilled in the art. Essentially, a bias source is not shown and the entire unit may be battery operated or may derive power from the AC lines as is conventional. It is also understood that the blood sample in cartridge 50 may be preheated by using an ordinary heating element incorporated in a temperature control system. The heating of a blood sample is conventional and can easily be accomodated by well-known circuitry which in essence is not considered as a part of this invention.

Essentially, the logic circuitry as depicted in FIG. 7 can be implemented by presently available integrated circuit components and may employ a conventional type of logic system such as TTL devices. See for example a text book entitled TTL Cookbook by D. E. Lancaster published by Howard W. Sams Co. (1974). This text book has many examples of suitable logic circuits which can be employed in the logic depicted in FIG. 7. Accordingly, the counter/display driver 75 and data comparator 76 may be implemented by an integrated circuit component designated as the ICM7217 sold by the Intersil, Inc. The latches as 71 may be implemented by utilizing a two input NANDgate quad circuit as the 7400 with two element arranged as a latch.

The switches and the remaining circuits are all available in integrated circuit form from a wide variety of sources. It is of course also understood that one can implement the above described logic functions by means of a microprocessor using a suitable program and hardware configuration. See a text entitled Microprocessor and Microcomputers by B. Soucek, published by John Wiley & Sons (1976).

Again, referring to FIG. 7 the operation of the analyzer system is as follows: Test cartridge 50 is fully inserted into the test well 41. The extending tab 48 and nozzle 52 protrude slightly from the test well to enable the operator to insert a syringe 31 containing a blood sample into the cartridge 50. The unit, of course, may provide a suitable prewarming period to allow the cartridge and therefore the blood sample to reach incubator temperature. As the blood sample enters the entry chamber 55 of cartridge 50, it is caused to flow along the lower most side of the test cartridge 50 as shown in FIG. 5A. Upon reaching each annular wall as 56 a pool of blood is formed in each test chamber until the depth of pool exceeds the height of the wall 56 whereby the blood overflows into the next chamber and so on.

When the blood sample reaches the overflow chamber 57, light from source 58 is blocked from sensor 59. When this occurs sensor 59 triggers the pulse generator 79. The triggering of generator 79 resets the logic enable latch 74, latches 71, latch 91 and the counter/display driver 75. The triggering of the enable latch 74 provides power to oscillator 77, motor 78 and the photosensors 63. In this manner, the counter 75 begins to count and the display 42 will display the count in seconds. The test cartridge 50 as coupled to the motor begins to rotate about its axis as shown in FIG. 6A. Light which is projected from sources 62 and received by photosensors 63 causes the data latches 71 to be held in the reset condition which is analogous to a no clot condition. Hence, the clot indicators 43 do not indicate the presence of the clot. However, as shown in FIG. 6B, when clotted blood blocks the light in a test chamber then the associated latch is caused to change state. Simultaneously, with the change of state, the particular clot indicator 43 is illuminated and the end point counter 72 detects this condition and increments one count for one latch operation. This also triggers latch 91 which enables data comparator 76 to control the enable latch 74.

The process of clot detection in other test chambers is continued until the analysis is terminated by the triggering of the logic enable latch 74. The latch 74 may be triggered by either the data comparators 73 or 76. When the latch 74 is triggered, the oscillator 77 is disabled as is motor 78 and the count stored in counter 75 is displayed by the display 42 in a constant manner. The state of latches 71 and the corresponding clot indicator lamps 43 are also preserved during this condition.

As indicated above, the setting of switches 44 and 45 establishes the mode of operation which will cause the tripping of the logic enable latch 74. For example, if the number of clots detected equals the setting of switch 45, then comparator 73 will trigger latch 74 and the time display on display 42 will be that time in which that number of clots occurred. If the number of clots does not equal the number of switch 45 but at least one clot has occurred then latch 74 will be triggered by comparator 76 through the ANDgate 81 and the time display will be the time preset by switch 44. If no clot has occurred then latch 91 is not set and the logic enable latch will not be reset to allow the analysis to continue until a clot is detected. At this time the latch will be tripped via comparator 76 as any time greater than the time set on switch 44 will cause a reset. Thus the time now displayed on display 42 is the time for at least one clot to occur. If no clot occurs within a reasonable time which may be preset and for example may be 800 seconds, then equipment is automatically deactivated by a suitable timeout.

A timeout provision is well-known in the art and may comprise a separate counter which will provide a signal to trigger latch 74 after a predetermined period as for example, 800 seconds. It is of course understood that if switch 92 is activated then the data comparator 76 will provide a pulse at the output at the time set by switch 44. Thus, the setting of thumbwheel switches 44 and 45 establishes the mode of operation of the analyzer. When switch 44 is set to all zeros the number set on switch 45 establishes the condition for the termination of the analyses. For example, assume switch 45 is set to 5 and switch 44 is set to 0000 and the test cartridge 50 has a blood sample but has no reagents. In this manner, the ten test chambers which contained blood are simultaneously monitored. The system then essentially performs ten identical coagulation time tests. The resulting time of termination of analysis after detecting five clots or end point approximates the average coagulation time for the ten tests.

Similarly, if switch 45 is set to 10(0) and switch 44 is set to 480 seconds and test cartridge has premeasured heparin in the test chambers such that the final heparin concentration of the blood heparin mixture in a given test chamber may be identified by the numeral product of a constant and the chamber number, then the analysis termination will be established by the setting of switch 44. At the conclusion of the 480 second time interval, the lowest number channel or chamber for which the clot indicator is not energized establishes the heparin concentration required to prolong coagulation to at least 480 seconds.

Similarly, assume for example that switch 45 is set to 10(0) and switch 44 to 135 seconds. The test cartridge has premeasured protamine in its test chambers such that the final protamine concentration of the blood-protamine mixture in a given test chamber is equal to the chamber number itself (i.e. the constant of proportionality is unity). Then at the conclusion of the 135 second time interval, if the lowest numbered chamber in which a clot has been detected is 3, the preferred protamine neutralizing dose for a patient with a 5700 ml blood volume is the product of 3 units per ml and 5700 ml or 17,000 units of protamine.

Thus as indicated, the above indicated system is extremely simple and absolutely reliable in operation as each chamber is monitored in the cartridge and clots are automatically detected and indicated by the equipment on the basis of the chamber number. The cartridge 50 as shown above is extremely rugged and simple to use as compared to any prior art cartridge and eliminates the need for an operator to distribute blood samples in individual compartments as done in many prior art devices. The logic circuitry employed such as the end point counter 72 assumes that each clot will be detected sequentially even though clots may occur at the same time. This is due to the scanning technique employed which assures that each latch as 71 is "locked at" at least once in each counter 75 count cycle.

According to FIG. 1 the user upon a detection of a clot in a test chamber can determine a patient's reagent needs by forming the product of the patient's blood volume and the concentration of reagent in the chamber. For example, assume the volume 12a is 0.5 ml, and heparin content premeasured into each chamber is equal to the product of the chamber number and 0.8 units of heparin (e.g. chamber number 4 contains 4×0.8 or 3.2 units of heparin). If after 480 seconds of analyzing a blood sample it is observed that no clots are formed in chambers 3, 4 and 5 and that the patient has a blood volume of 5700 ml. This is the blood volume for a male, 165 pounds, 5 feet, 10 inches according to Allen, et al.: "Prediction of blood volume and adiposity in man from body weight and cube of height" Metabolism 5: 328–345, 1956. Then the heparin dose required to prolong the patient's coagulation time to at least 480 seconds is equal to the product-chamber, 3; blood volume, 5700 ml; and constant, 0.8 units heparin/0.5 ml or 27,360 units of heparin.

It will be understood that the precision of such determination of heparin dose may be improved by increasing the number of test chambers with a proportionate reduction of the difference in heparin content between chambers. The ability of the observer to distinguish between clotted and unclotted blood, represents the practical limitation to such method of improving the analysis, according to FIG. 3.

I claim:

1. An article of manufacture for use as a blood specimen sample holder in performing optical analysis of the coagulation time of a blood sample, comprising:

a longitudinal tubular member fabricated from a transparent rigid plastic having a surface roughness adhesiveness for clotted blood to permit clotted blood to adhere to it, said longitudinal tubular member being symmetrically disposed about an axis and having a closed bottom and an opened top for receiving a blood sample, said member having a plurality of annular walls disposed about the inner surface to form a plurality of chambers with said walls each of a predetermined height and relatively concentric to form a blood sample passageway from the opened top to the closed bottom, whereby when a blood sample is introduced into said opened top and said member is tilted from the horizontal blood will flow into a first chamber until it is filled and overflow over said associated wall into the next chamber and so on until each of said chambers contains a sample pool of said blood.

2. The sampler holder according to claim 1, wherein said tubular member is a cylindrical member.

3. The sample holder according to claim 2, further including keying means coupled to said bottom closed surface and adapted to be engaged by drive means for rotating said tubular member.

4. The sampler holder according to claim 2, further including an extending tab located on said tubular member and extending above the top opening for allowing one to grasp said tab to lift said tubular member.

* * * * *